(12) United States Patent
Carlson et al.

(10) Patent No.: US 12,083,329 B2
(45) Date of Patent: Sep. 10, 2024

(54) SYSTEMS AND METHODS FOR CONTROLLING NEEDLE PENETRATION

(71) Applicant: Boston Scientific Scimed, Inc., Maple Grove, MN (US)

(72) Inventors: Steven T. Carlson, St. Paul, MN (US); Niraj P. Rauniyar, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 515 days.

(21) Appl. No.: 16/983,349

(22) Filed: Aug. 3, 2020

(65) Prior Publication Data

US 2021/0052827 A1 Feb. 25, 2021

Related U.S. Application Data

(60) Provisional application No. 62/890,367, filed on Aug. 22, 2019.

(51) Int. Cl.
| | |
|---|---|
| *A61M 5/46* | (2006.01) |
| *A61B 17/00* | (2006.01) |
| *A61B 17/34* | (2006.01) |
| *A61B 18/04* | (2006.01) |
| *A61M 5/32* | (2006.01) |

(52) U.S. Cl.
CPC ............ *A61M 5/46* (2013.01); *A61M 5/3287* (2013.01); *A61M 2005/3247* (2013.01)

(58) Field of Classification Search
CPC .................. A61M 5/46; A61M 5/3287; A61M 2005/3247; A61M 2210/1096; A61M 2210/166; A61B 17/3478; A61B 18/04; A61B 2017/00274; A61B 2017/00398; A61B 2018/00547; A61B 2018/048; A61B 2090/034
See application file for complete search history.

(56) References Cited

U.S. PATENT DOCUMENTS

| | | | |
|---|---|---|---|
| 3,659,610 A | 5/1972 | Cimber | |
| 4,512,767 A | 4/1985 | Denance | |
| 5,300,029 A | 4/1994 | Denance | |
| 2008/0269862 A1* | 10/2008 | Elmouelhi | ......... A61B 18/1492 74/519 |
| 2009/0234319 A1 | 9/2009 | Marksteiner | |

(Continued)

FOREIGN PATENT DOCUMENTS

WO    WO 2019/102484 A1    5/2019

OTHER PUBLICATIONS

International Search Report and Written Opinion in International Application No. PCT/US2020/044735, mailed Oct. 26, 2020 (13 pages).

*Primary Examiner* — Robert J Utama
*Assistant Examiner* — Hamza A Darb
(74) *Attorney, Agent, or Firm* — Bookoff McAndrews, PLLC

(57) ABSTRACT

A needle adjustment device is provided. The needle adjustment device includes a stopping component and an actuator. The stopping component is configured to establish a maximum penetration depth of a needle. The actuator is fixedly coupled to the needle and movable proximally and distally to one or more positions and to adjust a penetration depth of the needle depth up to the maximum penetration depth.

20 Claims, 7 Drawing Sheets

(56) References Cited

U.S. PATENT DOCUMENTS

| | | | |
|---|---|---|---|
| 2014/0276471 A1* | 9/2014 | Emery | A61B 17/8822 |
| | | | 606/93 |
| 2016/0074217 A1* | 3/2016 | Price | A61M 5/3287 |
| | | | 604/156 |
| 2016/0302824 A1* | 10/2016 | Sato | A61B 1/00 |
| 2018/0168712 A1* | 6/2018 | Hoey | A61B 18/04 |

* cited by examiner

SYSTEMS AND METHODS FOR CONTROLLING NEEDLE PENETRATION

CROSS-REFERENCE TO RELATED APPLICATIONS

This application claims the benefit of priority from U.S. Provisional Application No. 62/890,367, filed on Aug. 22, 2019, which is incorporated by reference herein in its entirety.

TECHNICAL FIELD

The present disclosure relates generally to medical systems, devices, and related methods. More specifically, the present disclosure relates to medical systems and/or devices for controlling needle penetration.

BACKGROUND

Medical devices such as transurethral devices may deploy a needle through a shaft to treat tissue in a patient. For example, transurethral devices may deliver steam to prostatic tissue to denature the tissue. The needle may be inserted transurethrally into the prostate tissue. Some such medical devices have needles that are controllable by a solenoid device that operates in a fully deployed configuration or a fully retracted configuration. The solenoid creates a magnetic field that drives a magnet back and forth depending on the magnetic field polarity (direction of current) as applied by the solenoid. The magnet may travel until it hits a stop at a distal end during deployment or against a stop at a proximal end of the solenoid during full retraction. In these devices, the solenoid (and thus the needle driven by the solenoid) cannot be maintained at a distance between full deployment and full retraction. These devices do not have a mechanism for variable needle penetration control, where needle penetration depth may reside be between the minimum needle penetration depth at the fully retracted configuration and the maximum needle penetration depth at the fully deployed configuration.

SUMMARY

According to an example, a needle adjustment system is provided. The needle adjustment system comprises a stopping component configured to establish a maximum penetration depth of a needle, and an actuator fixedly coupled to the needle and movable proximally and distally to one or more positions to adjust a penetration depth of the needle up to the maximum penetration depth.

In one example, the actuator moves to the stopping component to establish the maximum penetration depth. In another example, a driving component moves the actuator at least proximally or distally. The driving component may be configured to move the stopping component and the actuator together proximally or distally. The driving component may be manually adjustable. The driving component may be a spring configured to move the actuator distally. In one example, the driving component is a motor device configured to move the actuator. The actuator may further comprise a protrusion extending from a handle assembly to move the actuator. The needle may move in a needle retracting direction when the actuator moves in a proximal direction and the needle may move in a needle deployment direction when the actuator moves in a distal direction. The actuator may be movable by one or more of a spring, solenoid, pneumatic, or hydraulic actuation mechanism. The needle adjustment system may further comprise a motor device configured to engage a corresponding mating component of the actuator to move the actuator proximally and distally. The actuator may comprise a latch component configured to position the needle in a retracted position. The driving component may drive the actuator and the needle distally when the latch mechanism disengages. The driving component is configured to move both the actuator component and the driving component proximally and distally when the latch component is not engaged with the mating component. The needle adjustment system may further comprise a trigger configured to unlatch the latch mechanism when the trigger is engaged by an operator such that the driving component moves the actuator to the stopping component.

In another aspect, a needle insertion device comprises: a handle located at a proximal end of the device; a needle deployment trigger located proximate the handle; a shaft coupled to a distal end of the handle; a needle extending from the proximal end of the device to a distal end of the device; an actuator fixedly coupled to the needle and movable proximally and distally to one or more positions to adjust a penetration depth of the needle; and a hard stop component positioned to provide a maximum penetration depth for the needle.

The hard stop component may provide the maximum penetration depth for the needle when the actuator contacts the hard stop component at a proximal side of the hard stop component. The actuator may further comprise a protrusion extending from the handle to manually move the actuator proximally and distally. The actuator may be configured to move proximally and distally to move the needle to a variable penetration depth up to the maximum penetration depth. The needle adjustment device may further comprise a driving component to move the actuator at least one of proximally or distally. The driving component may be manually adjustable.

In yet another aspect, a needle driving component comprises a needle disposed proximally and distally; an actuator fixedly coupled to the needle and movable proximally and distally to one or more positions to adjust a penetration depth of the needle and including a latch component configured to engage a corresponding mating component; and a driving component affixed to the actuator and configured to drive movement of the actuator proximally and distally.

The driving component may drive the actuator and the needle distally when the latch mechanism disengages from the mating component. The driving component may be a spring. The driving component may be manually adjustable and may further comprise a protrusion to manually move the actuator and the hard stop component proximally and distally.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to systems, devices, and methods for needle actuation within a shaft of a medical device (e.g., a transurethral medical device). Reference will now be made in detail to examples of the present disclosure described above and illustrated in the accompanying drawings. Wherever possible, the same reference numbers will be used throughout the drawings to refer to the same or like parts.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value unless otherwise stated.

The terms "proximal" and "distal" are used herein to refer to the relative positions of the components of an exemplary medical device or medical insertion device. When used herein, "proximal" refers to a position relatively closer to the exterior of the patient or closer to a medical professional using the medical device or medical insertion device. In contrast, "distal" refers to a position relatively farther away from the medical professional using the medical device or medical insertion device, or closer to the interior of the patient.

Figure 1:
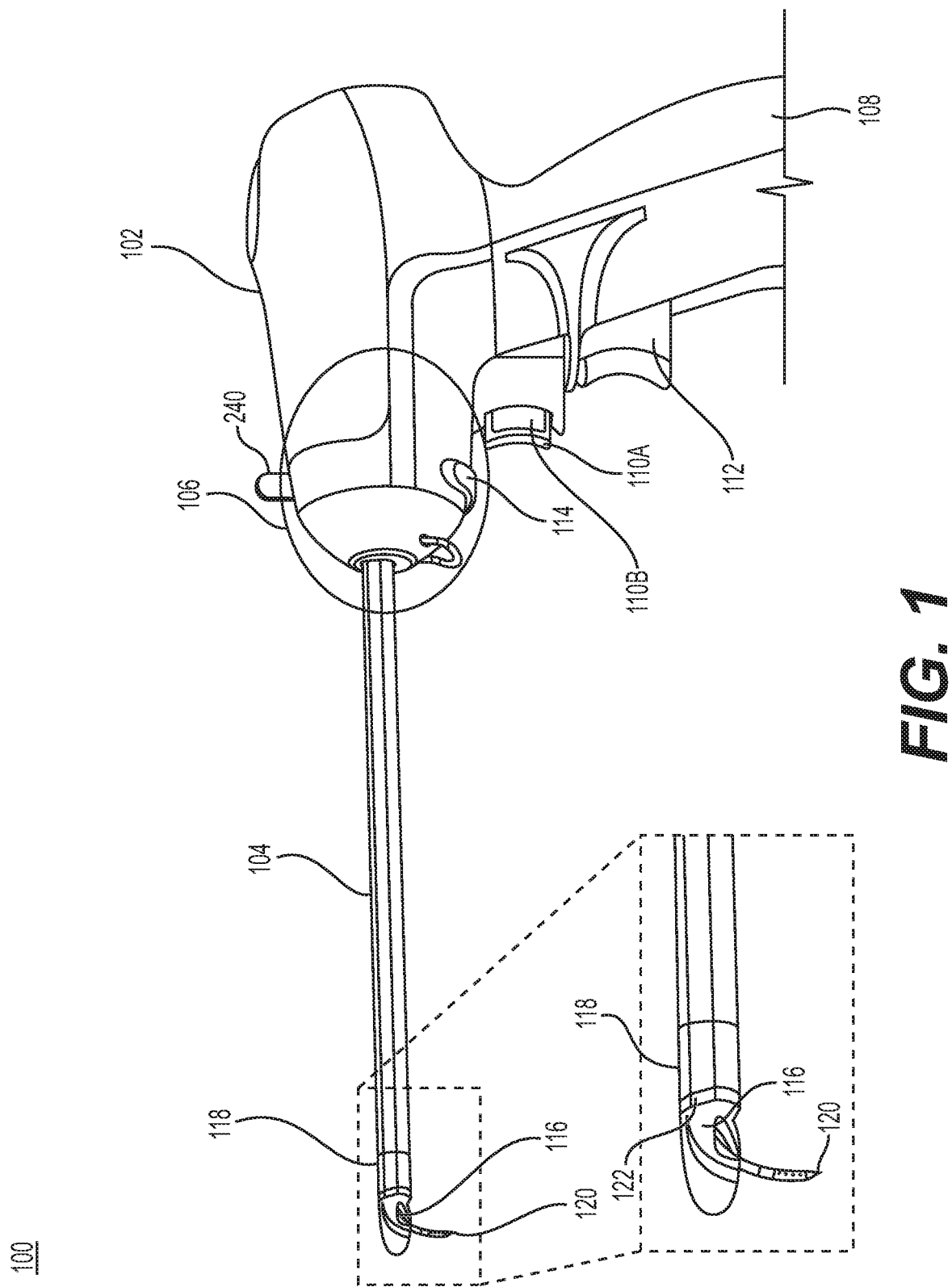
FIG. 1 illustrates a first example of a medical device including a needle actuation system, according to the present disclosure.

FIG. 1 illustrates a first example of a medical device with a needle actuation system of a medical device, according to the present disclosure. FIG. 1 shows the medical device at reference numeral 100. The medical device 100 includes a needle driving device 102 and a shaft 104. The needle driving device 102 comprises the needle actuation system, shown generally at reference numeral 106 and which is described in various aspects herein. The needle driving 102 also has a handle component ("handle") 108, a saline flush trigger 110A, a needle deployment trigger 110B, a vapor activation trigger 112, and a needle retraction button 114. The shaft 104 is a straight tube or member that contains within it a needle, shown at reference numeral 116. The needle driving device 102 also includes a driving component 240.

The shaft 104 interfaces with the medical device 100 to enable the medical device 100 to control insertion of the shaft 104 into a patient's body (e.g., transurethrally or through another orifice, incision, or cavity) and to actuate and control the needle 116 disposed within the shaft 104, e.g., by the needle actuation system 106. For example, as described by the techniques herein, the driving component 240 may be movable to enable manual actuation of the penetration depth of the needle 116 up to a maximum penetration depth. These actuation and control techniques of the needle 116 are described in more details herein. A proximal end of the shaft 104 is configured to interface with an opening at the distal end of the needle driving device 102. The distal end of the shaft 104, shown at reference numeral 118, is configured to be inserted into the patient's body. The needle 116 has a tip 120 at the distal end 118 of the shaft 104. In one example, the distal end 118 of the shaft 104 has an opening 122 enabling the tip 120 of the needle 116 at the distal end 118 to move in multiple directions, as controlled by an operator of the medical device 100. In one example, the needle 116 may extend from the distal end 118 of the shaft 104 at variable/varying penetration depths, as described by the techniques herein. In another example, the needle 116 may retract within the distal end 118 of the shaft 104 (e.g., to keep the needle covered/unexposed as the medical device 100 is navigated to the intended treatment location).

It is advantageous for the operator of the medical device 100 to control and actuate the needle 116 such that it can penetrate into the patient's body at various penetration depths. For example, the medical device 100 may be a device that is configured to deliver steam to tissue (e.g., prostatic tissue) and denaturize the tissue. The shaft 104 may be inserted into the patient's body transurethrally such that the tip 120 of the needle 116 is driven through the urethra and into prostate tissue.

The needle actuation system 106 in FIG. 1 enables manual control of the penetration depth of the needle 116 (also referred to as "needle penetration depth"). For example, as described by the techniques herein, the driving component 240 may be manually adjusted by an operator of the medical device 100 to vary the needle penetration depth.

Figure 2A:
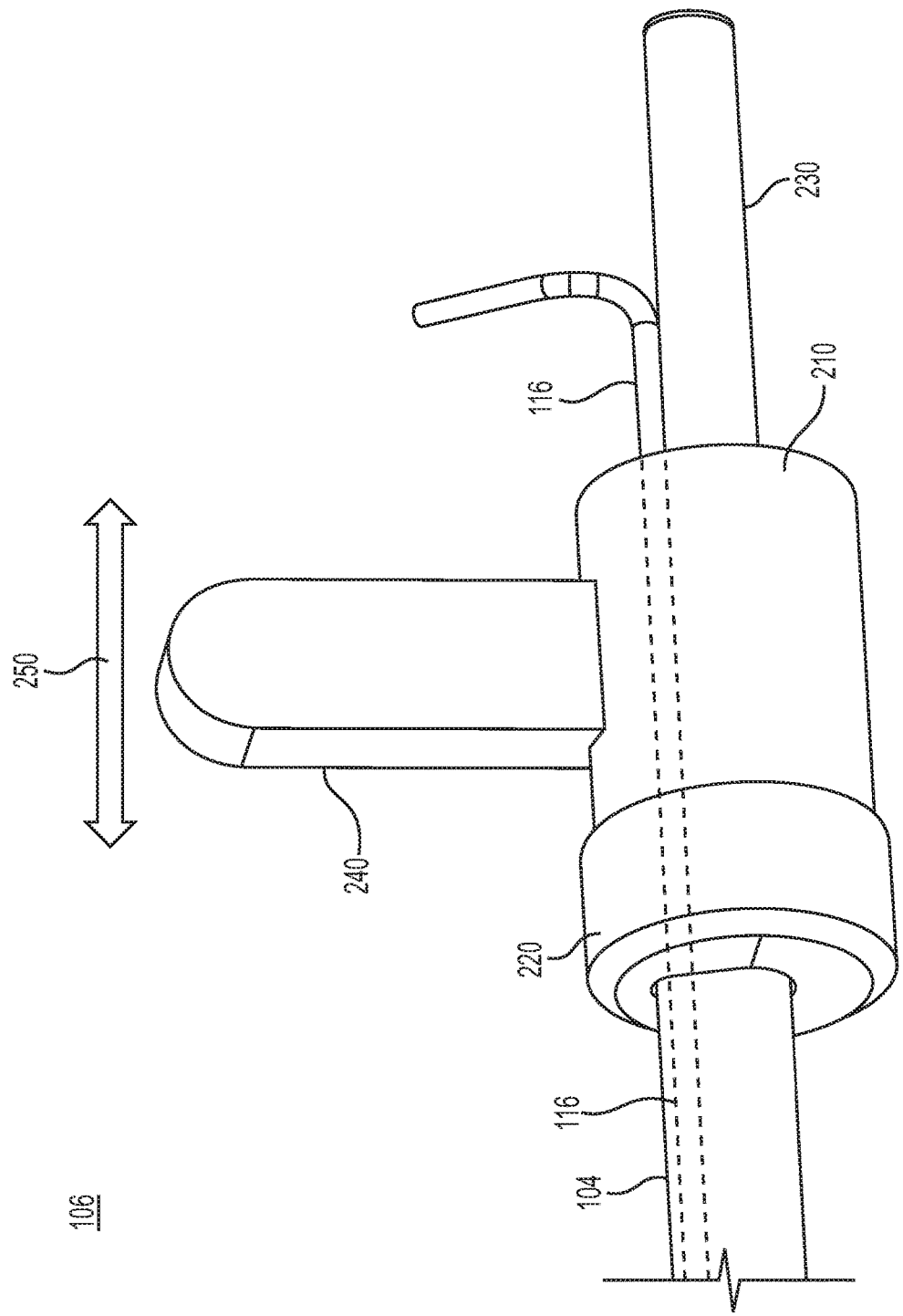
FIGS. 2A and 2B illustrate the needle actuation system of the medical device of FIG. 1 with manual control.
Figure 2B:
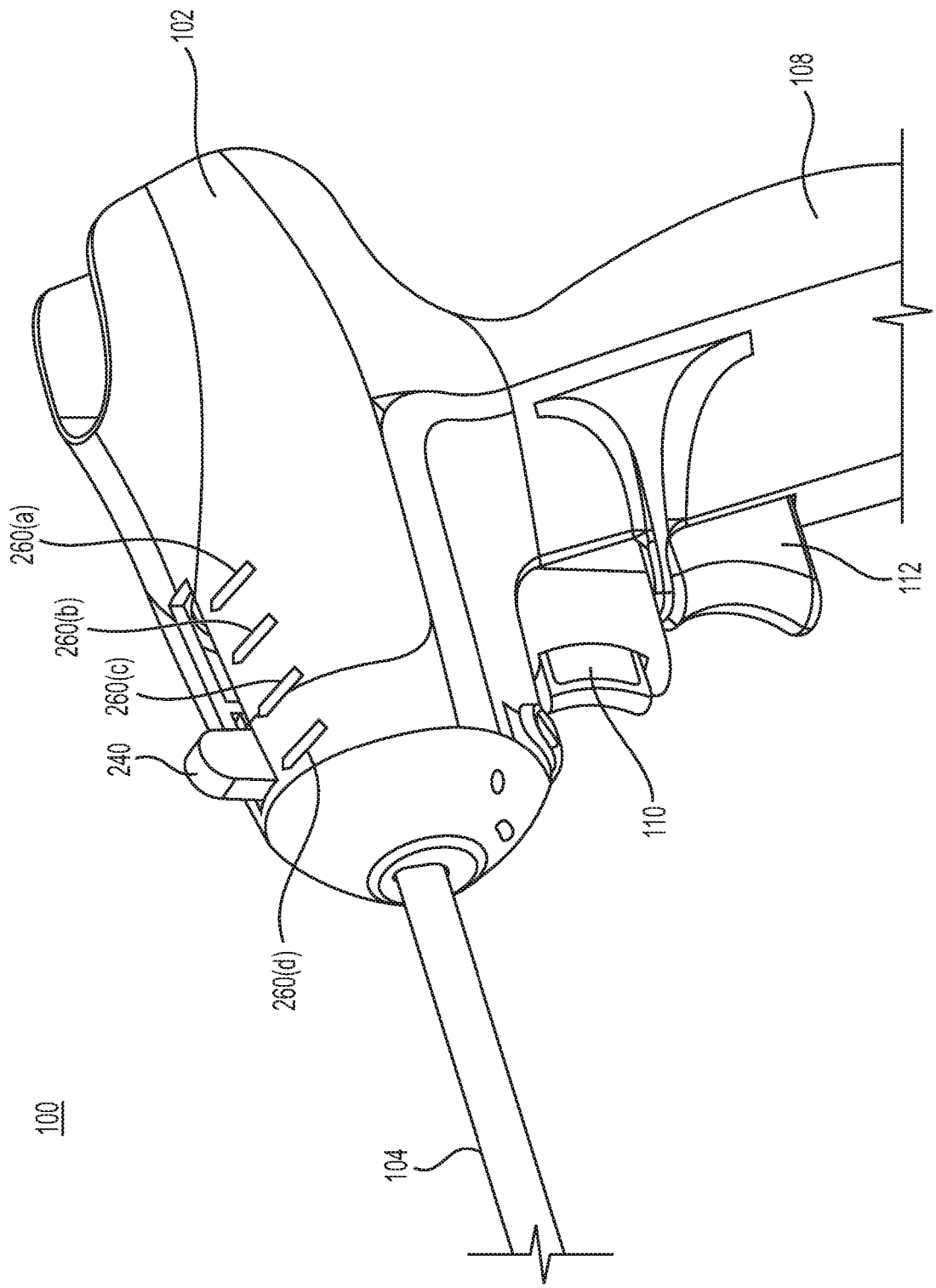

Reference is now made to FIGS. 2A and 2B. FIGS. 2A and 2B show the needle actuation system 106 of the medical device 100. The needle actuation system 106 is a manually controlled needle actuation system.

The needle actuation system 106 comprises an actuator 210, a hard stop component 220, the shaft 104, the needle 116, and a tube 230. The actuator 210 includes a driving component, shown at reference numeral 240, located at a top end of the actuator 210. The needle actuation system 106 is disposed at a distal end of the needle driving device 102, at a location within the needle driving device 102, as described in connection with FIG. 1.

Also described above in connection with FIG. 1, the shaft 104 is configured to extend from the distal end of the needle driving device 102 to the distal end 118. The tube 230 is disposed within the needle driving device 102 and is configured to interface with the shaft 104. The actuator 210 and the hard stop component 220 are configured to slide or slidingly reside on the tube 230. For example, the actuator 210 and the hard stop component 220 have an opening (not shown in FIG. 2A), through which the tube 230 is inserted (e.g., such that the actuator 210 and the hard stop component "wraps around" the tube 230). The needle 116 is fixedly attached to the actuator 210 and is configured to enter the shaft 104 via the opening of the actuator 210 through which the tube 230 is inserted. In one example, the needle 116 is flexible tubular member that is configured to be attached to a fluid source at a proximal end to deliver fluid through the needle 116 to the needle tip 120. The actuator 210 is configured to move along the tube 230. The movement of the actuator proximally and distally along an axis (also referred to herein as a longitudinal axis) is shown in FIG. 2A as the direction of actuation arrows at reference numeral 250. It should be appreciated that as the needle navigates to a tissue region of interest, the tip 120 of the needle 116 may rotate as the driving device 102 and the shaft 104 is rotated. As the actuator 210 moves along the direction of actuation 250, the needle 116 moves along with the actuator 210. Accordingly, as the actuator 210 moves in a proximal direction along the axis, the needle 116 also moves in the proximal direction, away from the distal end 118 of the shaft 104, and thus moves in a retracting direction. Similarly, as the actuator 210 moves in a distal direction along the axis, the needle 116 also moves in the distal direction toward the distal end 118 of the shaft 104, and thus moves in a deployment direction.

In one example, the hard stop component 220 is fixed (e.g., immovable in the direction of actuation 250) along the tube 230. The hard stop component 220 is located closer to a distal end of the tube 230 than the actuator 210. As the actuator 210 moves in the distal direction in along the axis, the actuator contacts the hard stop component 220 and thus, reaches a maximum movement location, where it cannot move further along the axis in the distal direction. Accordingly, when the actuator 210 contacts the hard stop component 220, the needle 116 reaches a maximum deployment position. In other words, the hard stop component 220 operates as a limiting barrier for movement of the actuator 210 and the needle 116 along the tube 230 in the distal direction of actuation 250 and sets a maximum needle penetration depth for the needle actuation system 206. The driving component 240 in FIG. 2A is used to manually move the actuator 210 along the tube 230. For example, an operator of the medical device 100 can hold the driving component 240 and physically move the actuator 210 in proximal direction of the direction of actuation 250 to move the needle 116 in a retracting direction and/or can move the actuator 210 in a distal direction of the direction of actuation 250 to move the needle 116 in a deployment direction up to a maximum deployment position when the actuator 210 contacts the hard stop 220.

Referring to FIG. 2B, the medical device 100 is shown with the driving component 240 shown extending out of a slot 242 at the top surface of the needle driving device 102. In one example, the driving component 240 has a protrusion that extends from a handle assemble to move the actuator 210. The slot 242 has a proximal end and a distal end. The proximal end of the slot 242 is the maximum proximal distance that the driving component 240 can travel. Likewise, the distal end is the minimum proximal distance that the driving component 240 can travel. FIG. 2B also shows a plurality of markings at reference numeral 260(a)-260(d). The markings 260(1)-260(d) may represent depth indicators of the needle 116. That is, when the driving component 240 is located proximate marking 260(a), the needle 116 may be extending through the shaft 104 at a first penetration depth (depending on the movement of the actuator 210), when the driving component 240 is located proximate marking 260(b), the needle 116 may be extending through the shaft 104 at a second penetration depth, and so on. Marking 260(d) may indicate a maximum penetration depth (e.g., the proximal end where the actuator 210 contacts the hard stop component 220) for the needle 116. Thus, an operator of the medical device 100 may be able to control the needle penetration by adjusting the driving component 240 to a location proximate an appropriate one of the markings 260(a)-260(d) (or to a location in between the markings 260(a)-260(d)). Upon adjustment by the operator, the driving component 240 stays in place along the shaft 230, for example, due to its friction fit on shaft 230 or via a spring connected to the driving component 240 and biased toward the retracted needle in the proximal most position of the driving component 240. Thus, in the manual operation described in connection with FIGS. 2A and 2B, an operator of the medical device 100 can manually control the needle 116 to various penetration depths. It should be appreciated that the other sensors, such as potentiometers or other position sensors, could be combined with the needle actuation system 206 to provide additional feedback on needle penetration depth to the operator of the medical device 100 or to an external controller to the medical device 100.

Figure 3A:
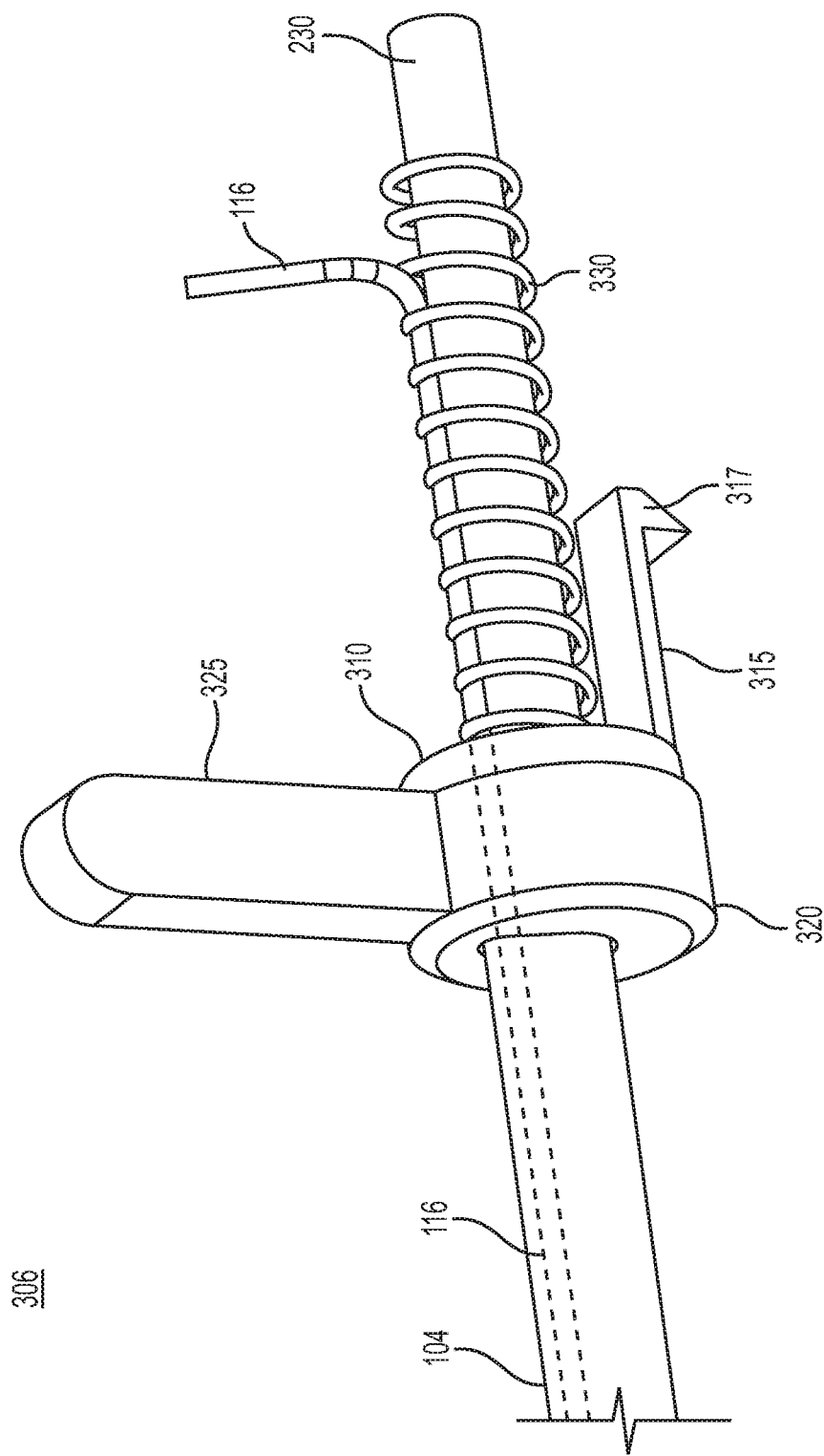
FIGS. 3A and 3B illustrate another example of a medical device with an example of the needle actuation system with partial active control.
Figure 3B:
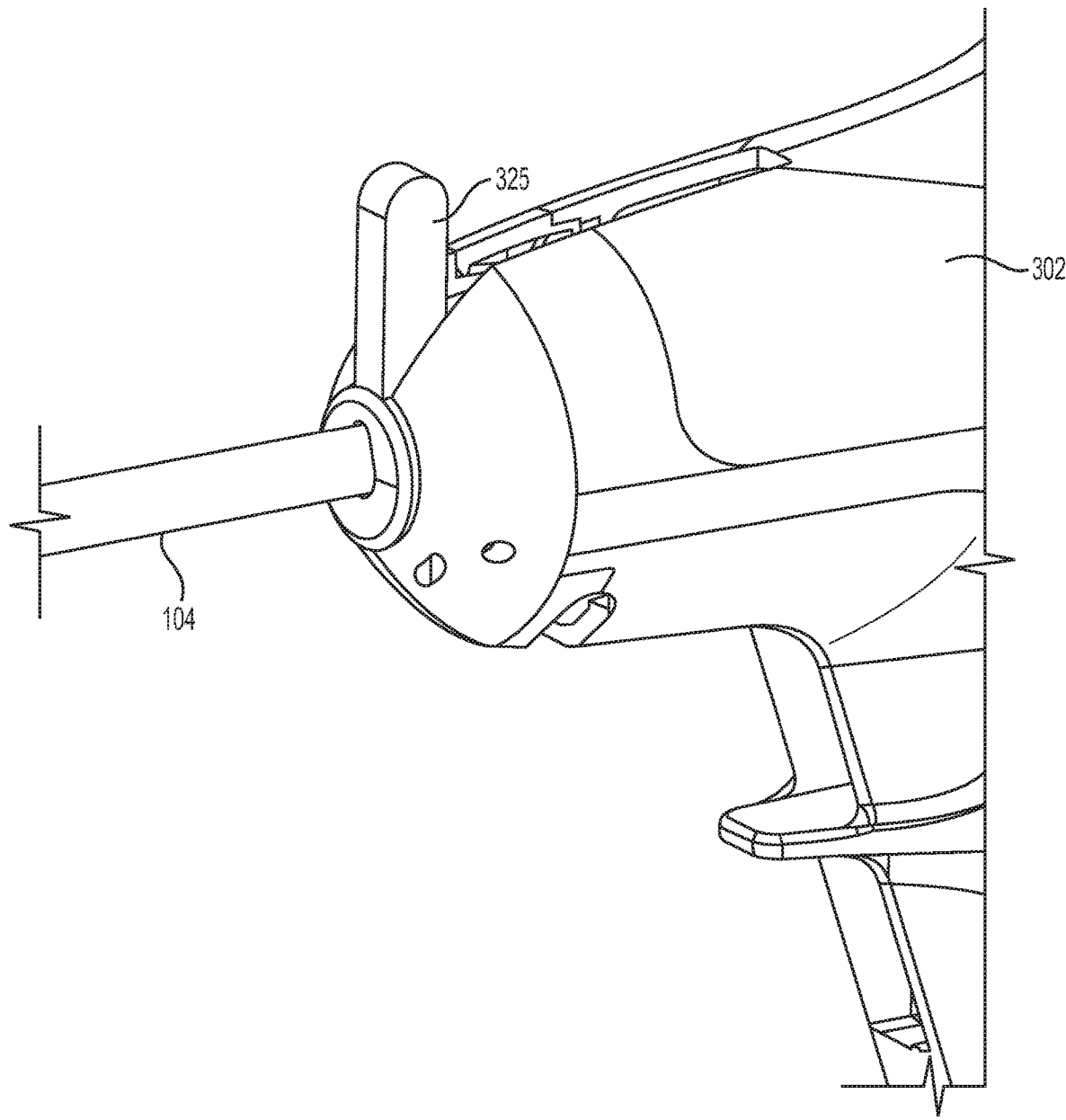

Reference is now made to FIGS. 3A and 3B. FIGS. 3A and 3B show another example of a medical device with a needle actuation system 306 having partial active control. The needle actuation system 306 comprises an actuator 310, a hard stop component 320, the shaft 104, the needle 116, the tube 230, and a spring 330. The shaft 104, the needle 116, and the tube 230 operate in a similar manner as described in connection with FIG. 2A above. The actuator 310 has a latch component (latch) 315 that is located on a bottom end of the actuator 310 and that extends, for example, in a proximal direction along the axis of the tube 230. The latch 315 has a hook or an extending unit, shown at reference numeral 317 in FIG. 3A that is configured to interface with a corresponding mating opening (not shown in FIG. 3A) on the driving device 102. The hard stop component has a driving component 325.

In FIG. 3A, both the actuator 310 and the hard stop component 320 are movable along the tube 230. For example, an operator of the medical device 100 may move the hard stop component 320 and the actuator 310 in FIG. 3A along the tube 230 by adjusting the driving component 325 in a direction of actuation (e.g., the direction of actuation 250). Thus, the operator can adjust the hard stop component 320 and the actuator 310 in a proximal direction and a distal direction along the tube 230 in the direction of actuation 250.

In one example, a proximal end of the hard stop component 320 is configured to mate or otherwise interface with or contact a distal end of the actuator 310 such that when the driving component 325 is adjusted in a proximal direction, the actuator 310 may move along with hard stop component when the actuator 310 is connected with or contacts the hard stop component 320 (e.g., the hard stop component 320 and the actuator 310 are "pulled back" in a retracting position in a proximal direction by moving the driving component 325 proximally). The hook 317 of the latch 315 engages a corresponding mating opening (not shown in FIG. 3A) and holds the hard stop component 320 and the actuator 310 in place. The needle 116 is connected to the actuator 310 in a manner similarly described in connection with FIG. 2A.

The spring 330 resides on the tube 230 (e.g., wrapped around the tube 230 and a portion of the needle 116). The spring 330 is immovably fixed to the tube on its proximal end and is connected to the actuator 310 on its distal end. Thus, as the actuator 310 moves in a proximal direction along the axis (e.g., due to movement of the hard stop component 320), the spring 330 compresses as it stays affixed to the actuator 310, and as the actuator 310 moves in distal direction along the axis, the distal end of the spring 330 stretches or expands as it stays affixed to the actuator 310.

The needle actuation system 306 in FIG. 3A enables partial active control and partial manual control of the penetration depth of the needle 116. In one example, an operator manually adjusts the hard stop component 320 in a proximal direction by adjusting the driving component 325 until the hook 317 of the latch 315 of the actuator 310 engages a corresponding mating opening (not shown in FIG. 3A). In this configuration, the actuator 310 and hard stop component 320 are secured to the driving device 102 via the hook 317 in the mating opening, and spring 330 is compressed in the proximal direction due to the movement and locked-in position of the actuator 310 in the proximal direction. Once the hook 317 engages the mating opening, the operator of the medical device may move the hard stop component 320 in the distal direction by adjusting the driving component 325 in the distal direction. In this example, when the driving component 325 is moved in the distal direction, the hard stop component 320 separates from the actuator 310, and the driving component 325 and hard stop component 320 move in the distal direction along the tube 230. The hard stop component 320 may be adjusted along the tube 230 by an operator to control the needle penetration depth as the needle is deployed. For example, the operator of the medical device may activate a release mechanism, such as the needle deployment trigger 110B shown in FIG. 1, and as the operator pulls the needle deployment trigger 110B, the latch 315 is configured to move such that the hook 317 of the latch 315 is no longer interfaced with the mating opening. When the hook 317 is released from the mating opening, the actuator 310 is no longer fixed to that specific location, and the spring 320 expands in the distal direction. As the spring 330 expands, it pushes the actuator 310 until the actuator 310 contacts the hard stop component 320 to the maximum needle penetration depth. The driving component 325 can then be adjusted to adjust the needle penetration depth. Since the needle 116 is affixed to the actuator 310, the needle 116 moves at the actuator 310 moves. Thus, in this example, the spring 330 operates as the driving mechanism for the needle 116. It should be appreciated that the spring 330 may be replaced by other driving mechanisms, such as a solenoid, pneumatics, hydraulics, or other actuation mechanism. In other words, in one example, the operator of the medical device may pull the driving component 325 in the proximal direction until the hook 317 interfaces with the mating opening, thus securing the actuator 310 and the hard stop component 320 in a first location. Then, the operator may separate the hard stop component 320 from the actuator 310 by moving the driving component 325 in the distal direction, such that the actuator remains latched in the first location and the hard stop component 320 is moved to a second location in a distal direction from the first location. The hard stop component 320 may be fixed in the second location by friction or by any other mechanism (e.g., a screw that secures the hard stop component 320 and the driving component 325 in the second location). When the spring 330 fires (e.g., when trigger 110B is pulled), the spring 330 pushes the actuator 310 from the first location until the actuator 310 contacts the hard stop component 320 in the second location. Thus, the hard stop component 320 can be moved to set a desired needle penetration depth.

FIG. 3B shows the medical device described in connection with FIG. 3A at reference numeral 350. The medical device 350 has the driving component 325 extending out of a slot at the top surface of the needle driving device 102. In one example, the driving component 325 has a protrusion that extends from a handle assembly to move the actuator 310. The needle driving device 102 in FIG. 3B is the same as that described in FIG. 1 above. As described above, the operator may initially adjust the driving component 325 in the proximal direction to engage the latch 315. When the latch in engaged, the operator then moves the driving component 325 in a distal direction to set the hard stop component 320 at the desired needle penetration depth. When the user pulls the trigger (not shown in FIG. 3B), the spring 330 drives the needle 116 to the hard stop component 320 (e.g., the desired needle penetration depth).

Figure 4A:
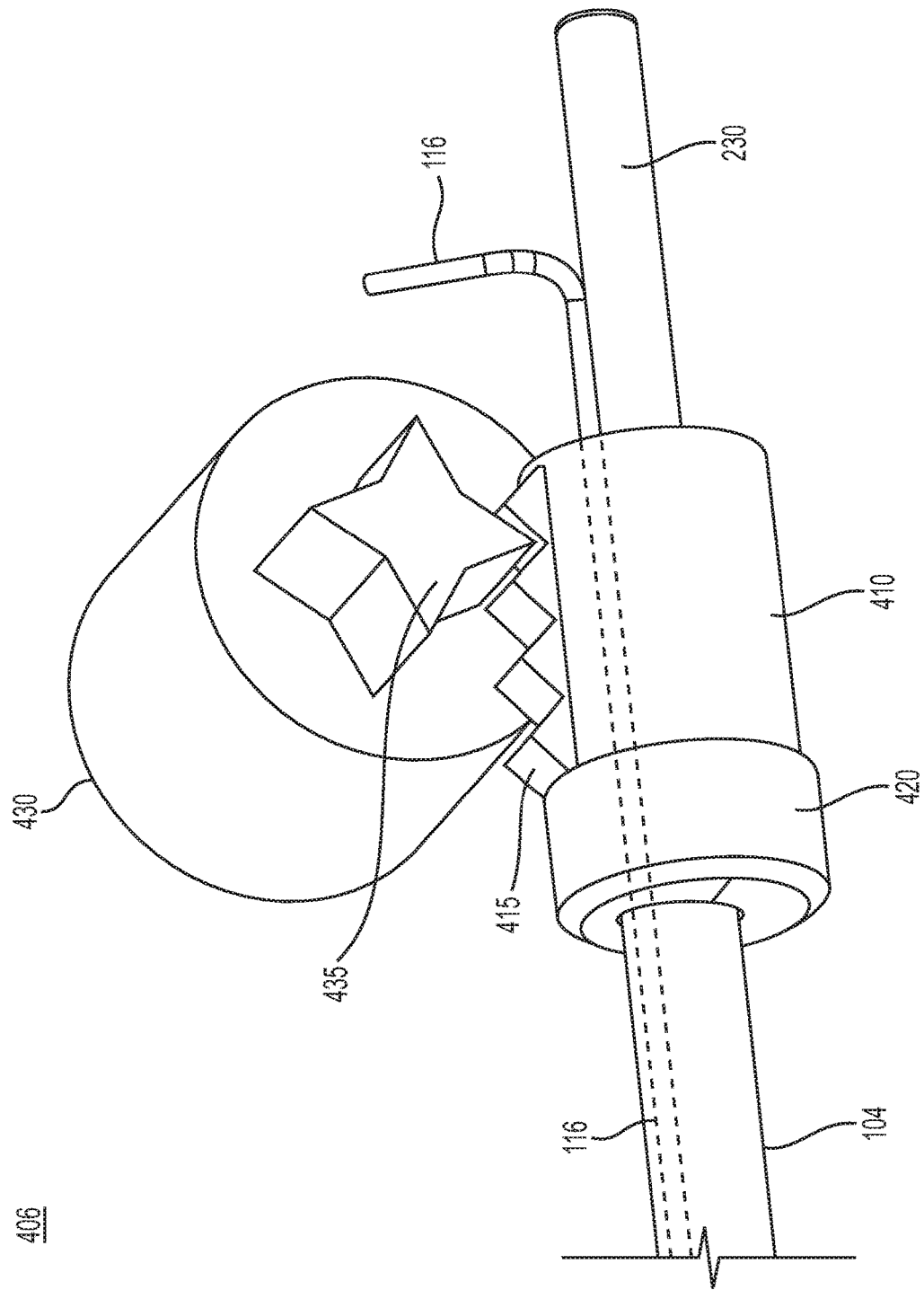
FIGS. 4A and 4B illustrate yet another example of a medical device with a third example of the needle actuation system with full active control.
Figure 4B:
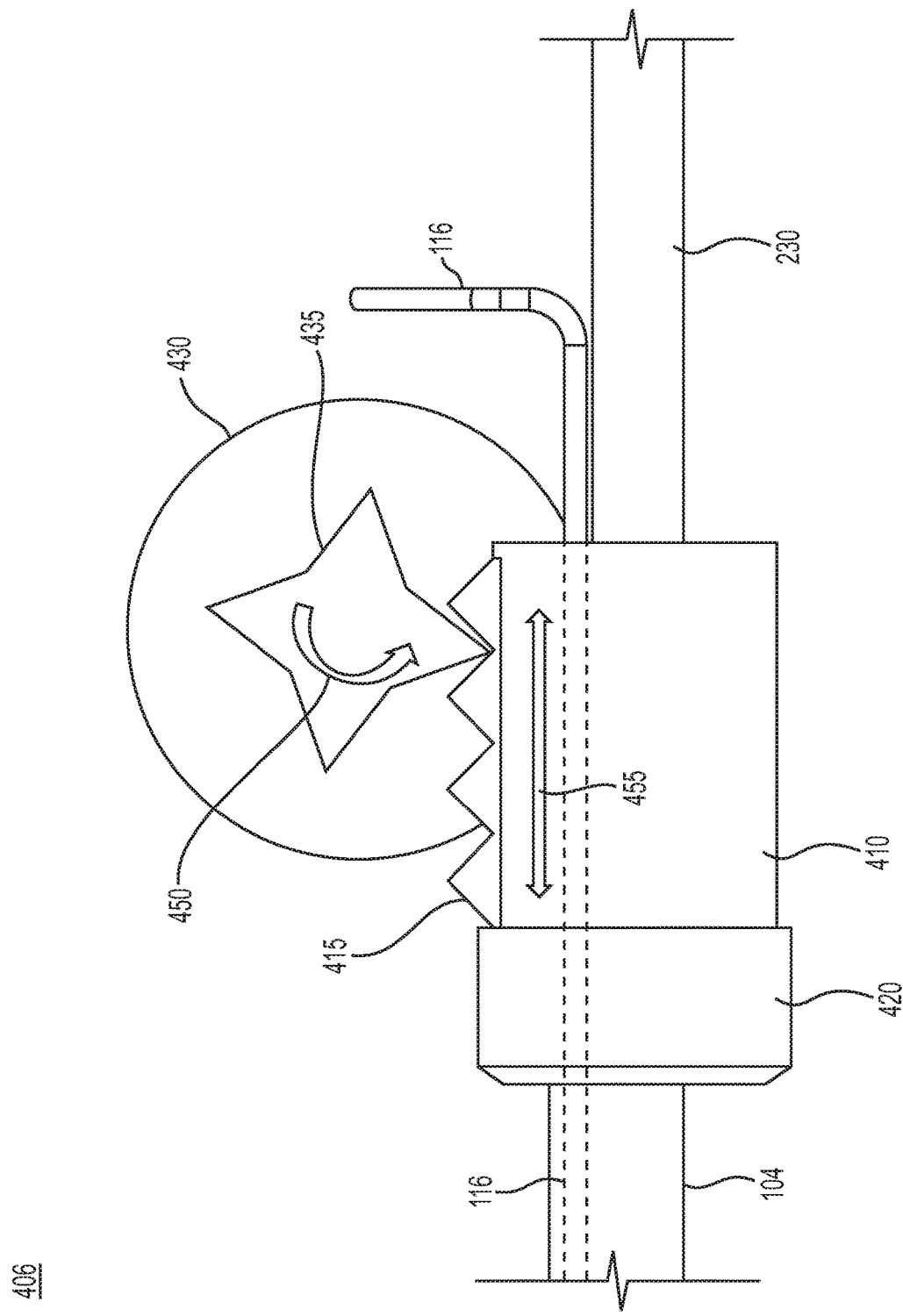

Reference is now made to FIGS. 4A and 4B. FIGS. 4A and 4B shown another example of a medical device with a needle actuation system in a full active control. In FIG. 4A, the needle actuation system is shown at reference numeral 406. The needle actuation system 406 comprises an actuator 410, a hard stop component 420, an active driving component 430, the needle 116, the shaft 104, and the tube 230. The needle 116, the shaft 104, and the tube 230 are the same as described in connection with FIGS. 1, 2A, 2B, 3A and 3C above. The active driving component 430 has an engagement component 435. In one example, the active driving component 430 is a motor, and the engagement component 435 is a gear. It should be appreciated that though a motor mechanism is described herein, the techniques could apply other powered controlled mechanisms, for example, pneumatics, hydraulics, etc.

The engagement component 435 is configured to engage the actuator 410 at a receiving portion of the actuator 410, shown at reference numeral 415 in FIG. 4A. In the motor example, the gear engages with the receiving portion 415 of the actuator 410, and the motor turns the gear to enable movement of the actuator 410 in a proximal and distal direction along the axis. For example, the motor may cause the gear to turn in a first direction (e.g., a counterclockwise direction) causing the actuator 410 to move in the proximal direction, and the motor may cause the gear to turn in a second direction (e.g., a clockwise direction) causing the actuator 410 to move in the distal direction. Since the needle 116 is affixed to the actuator 410 (in a manner similar to that described in connection with FIGS. 2A and 3A above), the needle 116 moves in a retracting direction as the actuator 410 moves in the proximal direction and moves in a deployment direction as the actuator 410 moves in the distal direction. The hard stop component 420 functions as a maximum distance along the tube 230 where the gear can move the actuator 410, and thus, the location of the hard stop component 420 sets a maximum the needle penetration depth. In one example, the hard stop component 420 may not be required in the needle actuation system 406. For example, an external controller may activate the motor and the gear to move the needle 116 in to a precise needle penetration depth without being limited to a maximum needle penetration depth defined by the hard stop component 420.

FIG. 4B shows the movement of the gear depicted at arrow 455 and the subsequent movement of the actuator 410 and needle 116 along the axis at arrow 460. In one example, the motor may be controlled automatically by a system configured with desired needle depth penetration information. For example, a computing system may be pre-programed with information about a desired needle depth penetration for the medical device during a medical procedure, and the motor may automatically drive the actuator 410 to accomplish precise needle depth penetration. Additionally, electrical feedback may be provided to a controller external to the needle actuation system 406.

It is desirable for an operator of medical device to be able to adjust needle penetration depth such that different tissue depths (e.g., prostate tissue depth) can be targeted by the medical device for treatment. The techniques described herein may be used to penetrate a needle to variable depths informed by imaging data, such as magnetic resonance imaging (MRI) or ultrasound data, for various treatment procedures (e.g., penetration to the edge of a prostate to treat maladies such as cancerous tissue). Operators of the medical device (e.g., physicians and medical professionals) thus can customize medical therapies by varying the penetration depth of the needle.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A needle adjustment device, comprising:
   a handle located at a proximal end of the device, the handle including a needle deployment trigger;
   a stopping component configured to establish a maximum penetration depth of a needle extending at least partially through the handle, wherein the stopping component is longitudinally movable relative to a housing of the handle to adjust the maximum penetration depth; and
   a first actuator coupled to the needle and configured to move the needle between a retracted configuration and a plurality of extended configurations, wherein each of the plurality of extended configurations has a different maximum penetration depth, wherein the first actuator includes a latch mechanism, and wherein the latch mechanism is configured to selectively retain the first actuator in the retracted configuration; and
   a second actuator coupled to the stopping component and configured to move the stopping component and the latch mechanism proximally to engage the latch mechanism and retain the first actuator in the retracted configuration.

2. The needle adjustment device of claim 1, wherein the second actuator is manually adjustable.

3. The needle adjustment device of claim 1, wherein the stopping component is longitudinally movable among a plurality of positions corresponding to the respective plurality of extended configurations having different penetration depths.

4. The needle adjustment device of claim 3, wherein the second actuator is configured to move the stopping component among the plurality of positions.

5. The needle adjustment device of claim 3, wherein the needle deployment trigger is configured to unlatch the latch mechanism and move the first actuator distally.

6. The needle adjustment device of claim 1, wherein the latch mechanism includes a hook.

7. The needle adjustment device of claim 6, wherein the latch mechanism is engaged upon the hook being received within an opening.

8. The needle adjustment device of claim 1, wherein, in a configuration in which the latch mechanism is engaged, the second actuator is configured to move the stopping component distally to establish the maximum penetration depth of the needle.

9. A needle insertion device, comprising:
   a handle located at a proximal end of the device, the handle including a needle deployment trigger;
   a shaft coupled to a distal end of the handle;
   a needle extending through at least a portion of the shaft and through at least a portion of the handle;
   an actuator coupled to the needle; and
   a hard stop component positioned to provide a maximum penetration depth for the needle, wherein the needle is configured to move between a retracted position and a first extended position and between the retracted position and a second extended position, wherein the needle has a greater maximum penetration depth in the first extended position than in the second extended position;
   wherein the actuator includes a latch mechanism, and wherein the latch mechanism is configured to selectively retain the actuator in the retracted position, and wherein the needle deployment trigger is configured to unlatch the latch mechanism and move the actuator distally.

10. The needle insertion device of claim 9, wherein the hard stop component provides the maximum penetration depth for the needle when the actuator contacts the hard stop component at a proximal side of the hard stop component.

11. The needle insertion device of claim 9, wherein the actuator is a first actuator, the device further comprising a second actuator coupled to the hard stop component, wherein the second actuator comprises a protrusion extending from the handle to manually move the second actuator proximally and distally.

12. The needle insertion device of claim 9, wherein the hard stop component is movable relative to a housing of the handle and relative to the actuator to adjust the maximum penetration depth.

13. The needle insertion device of claim 9, wherein the actuator is a first actuator, and wherein moving a second actuator proximally is configured to move the latch mechanism proximally.

14. The needle insertion device of claim 13, wherein, in a configuration in which the latch mechanism is engaged, the second actuator is configured to move the hard stop component distally to establish the maximum penetration depth of the needle.

15. The needle insertion device of claim 9, wherein the latch mechanism includes a hook.

16. The needle insertion device of claim 15, wherein the latch mechanism retains the actuator in the retracted position upon hook being received in an opening.

17. A needle insertion device, comprising:
   a handle located at a proximal end of the device, the handle including a needle deployment trigger;
   a needle having a portion extending at least partially through the handle, wherein the needle is coupled to a first actuator and configured to move proximally and distally between a retracted position and a fully extended position, wherein, in the fully extended position, the needle extends from a distal tip of a shaft at a penetration depth; and
   a second actuator coupled to a stop component and movable proximally and distally relative to a housing of the handle among a plurality of positions to adjust a maximum penetration depth of the needle, wherein the stop component provides the maximum penetration depth for the needle when the first actuator contacts the stop component at a proximal side of the stop component;
   wherein the first actuator includes a hook configured to selectively retain the first actuator in the retracted position, wherein a proximal movement of the second actuator causes the hook to move proximally so as to retain the first actuator in the retracted position, and wherein the needle deployment trigger is configured to unlatch the hook and move the first actuator distally.

18. The needle insertion device of claim 17, wherein the second actuator comprises a protrusion to manually to move the stop component coupled to the second actuator proximally and distally.

19. The needle insertion device of claim 17, wherein the first actuator is movable relative to the second actuator.

20. The needle insertion device of claim 17, wherein the hook is configured to be received in an opening to selectively retain the first actuator in the retracted position, and wherein, in a configuration in which the hook retains the first actuator in the retracted position, the second actuator is configured to move the stop component distally to establish the maximum penetration depth of the needle.

* * * * *